US012567142B2

(12) United States Patent
Jażdżyk et al.

(10) Patent No.: US 12,567,142 B2
(45) Date of Patent: Mar. 3, 2026

(54) AUTOMATED ORGAN SEGMENTATION OUTPUT QUALITY ASSESSMENT

(71) Applicant: GE Precision Healthcare LLC, Wauwatosa, WI (US)

(72) Inventors: Jakub Jażdżyk, Cracow (PL); László Ruskó, Budapest (HU); Borbála Deák-Karancsi, Budapest (HU); Vanda Czipczer, Budapest (HU); Fei Mian, Libertyville, IL (US); István Megyeri, Szeged (HU)

(73) Assignee: GE Precision Healthcare LLC, Waukesha, WI (US)

( * ) Notice: Subject to any disclaimer, the term of this patent is extended or adjusted under 35 U.S.C. 154(b) by 593 days.

(21) Appl. No.: 18/068,871

(22) Filed: Dec. 20, 2022

(65) Prior Publication Data

US 2023/0306590 A1    Sep. 28, 2023

Related U.S. Application Data

(63) Continuation-in-part of application No. 17/656,171, filed on Mar. 23, 2022, now Pat. No. 12,307,675.

(51) Int. Cl.
  *G06T 7/00*      (2017.01)
  *G16H 30/40*     (2018.01)
(52) U.S. Cl.
  CPC ........... *G06T 7/0012* (2013.01); *G16H 30/40* (2018.01); *G06T 2207/10081* (2013.01)
(58) Field of Classification Search
  CPC ..................... G06T 7/0012; G06T 7/11; G06T 2207/10056; G06T 2207/10068;
  (Continued)

(56) References Cited

U.S. PATENT DOCUMENTS 7,672,497 B2    3/2010  Nicponski
7,702,153 B2    4/2010  Hong et al.
             (Continued)

FOREIGN PATENT DOCUMENTS

CN      108399354 A     8/2018
CN      108847286 A     11/2018
             (Continued)

OTHER PUBLICATIONS

Cardenas et al., "AAPM RT-MAC Grand Challenge 2019", Cancer Imaging Archive Website, Available Online https://wiki.cancerimagingarchive.net/display/PublicIAAPM-FRT-MAC-FGrand+Challenge+2019#501359164dc5f53338634b35a3500cbed18472e0, 2019, 3 pages.

(Continued)

*Primary Examiner* — Ajibola A Akinyemi
(74) *Attorney, Agent, or Firm* — Amin, Turocy & Watson, LLP

(57)        ABSTRACT

An automated post-processing tool to assess the quality of deep learning-based organ segmentation in medical images is described. According to an example, a method comprises determining, by a system comprising a processor, current values of defined features of respective segmentation masks generated for different anatomical structures included in medical image data via auto-segmentation of the medical image data. The method further comprises determining, by the system, respective measures of correspondence between the current values and corresponding reference values determined for the defined features, determining one or more measures of quality of the auto-segmentation based on the respective measures of correspondence, generating quality assessment report data for the auto-segmentation comprising the one or more measures of quality in standard format that can be displayed by standard clinical software.

20 Claims, 10 Drawing Sheets

(58) Field of Classification Search

CPC . G06T 2207/10116; G06T 2207/10132; G06T 2207/30004; G06T 2200/24; G06T 2207/10072; G06T 2207/30041; G06T 2207/30168

USPC ........................................................ 382/128

See application file for complete search history.

(56) References Cited

U.S. PATENT DOCUMENTS

| | | | |
|---|---|---|---|
| 9,990,712 B2 | 6/2018 | Gazit | |
| 10,388,020 B2 | 8/2019 | Guo et al. | |
| 10,751,548 B2 | 8/2020 | Han | |
| 10,825,168 B2 | 11/2020 | Tegzes et al. | |
| 10,878,219 B2 | 12/2020 | Zhou et al. | |
| 2016/0321512 A1 | 11/2016 | Sarachan et al. | |
| 2017/0178320 A1* | 6/2017 | Saalbach | G06T 7/0012 |
| 2017/0213067 A1 | 7/2017 | Padmanabhan et al. | |
| 2022/0044412 A1* | 2/2022 | Yang | G06F 18/214 |
| 2022/0254029 A1 | 8/2022 | Vorontsov et al. | |
| 2022/0398718 A1 | 12/2022 | Rao | |
| 2023/0306590 A1 | 9/2023 | Jazdzyk et al. | |
| 2024/0265667 A1 | 8/2024 | Luciano et al. | |

FOREIGN PATENT DOCUMENTS

| | | | |
|---|---|---|---|
| CN | 114119474 A | 3/2022 | |
| EP | 3 889 888 A1 | 10/2021 | |
| WO | 9904690 A1 | 2/1999 | |
| WO | 2006064470 A2 | 6/2006 | |
| WO | 2015069827 A2 | 5/2015 | |
| WO | 2022/051290 A1 | 3/2022 | |

OTHER PUBLICATIONS

Cardenas et al., "Head and Neck Cancer Patient Images for Determining Auto-segmentation Accuracy In T2-weighted Magnetic Resonance Imaging Through Expert Manual Segmentations", Medical Physics, vol. 47, No. 5, Jun. 2020, 9 pages.

Rusko et al., "Deep-Learning-based Segmentation of Organs-as-Risk in the Head for MR-assisted Radiation Therapy Planning", Proceedings of the 14th International Joint Conference on Biomedical Engineering Systems and Technologies, Bioimaging, vol. 2, 2021, pp. 31-43.

Cheng et al., 'An automatic quality evaluator for video object segmentation masks', Measurement, vol. 194, pp. 1-11, May 15, 2022, 11 pages.

International Application No. PCT/US2023/080943 filed on Nov. 22, 2023, International Search Report and Written Opinion issued Mar. 27, 2024, 10 pages.

Jadhav| "What is t-SNE," https://medium.com/analytics-vidhya/what-is-t-sne-37bfb920e431, Analytics Vidhya, Jul. 20, 2020, 5 pages.

Chen, X. et al. | "CNN-Based Quality Assurance for Automatic Segmentation of Breast Cancer in Radiotherapy." Frontiers in Oncology, Apr. 1, 2020, vol. 10, Article 524, doi: 10.3389/fonc.2020.00524, 9 pages.

Soberanis-Mukul, R. D. et al. | "Uncertainty-based Graph Convolutional Networks for Organ Segmentation Refinement." Proceedings of Machine Learning Research, Under Review:1-15, 2020, 15 pages.

Non-Final Office Action received for U.S. Appl. No. 17/656,171 dated Oct. 17, 2024, 7 pages.

Notice of Allowance received for U.S. Appl. No. 17/656,171 dated Feb. 3, 2025, 8 pages.

* cited by examiner

Example Multi-Feature Segmentation Data

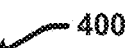

400

```
┌─────────────────────────────────────────────────────┐
│ DETERMINING, BY A SYSTEM COMPRISING A PROCESSOR,      │
│ CURRENT VALUES OF DEFINED FEATURES OF RESPECTIVE      │      402
│ SEGMENTATION MASKS GENERATED FOR DIFFERENT            │
│ ANATOMICAL STRUCTURES INCLUDED IN MEDICAL IMAGE       │
│ DATA VIA AUTO-SEGMENTATION OF THE MEDICAL IMAGE       │
│ DATA                                                  │
└─────────────────────────────────────────────────────┘
```

```
┌─────────────────────────────────────────────────────┐
│ DETERMINING, BY THE SYSTEM, RESPECTIVE MEASURES OF    │
│ CORRESPONDENCE BETWEEN THE CURRENT VALUES AND         │      404
│ CORRESPONDING REFERENCE VALUES DETERMINED FOR         │
│ THE DEFINED FEATURES                                  │
└─────────────────────────────────────────────────────┘
```

```
┌─────────────────────────────────────────────────────┐
│ DETERMINING, BY THE SYSTEM, ONE OR MORE MEASURES OF   │      406
│ QUALITY OF THE AUTO-SEGMENTATION BASED ON THE         │
│ RESPECTIVE MEASURES OF CORRESPONDENCE                 │
└─────────────────────────────────────────────────────┘
```

```
┌─────────────────────────────────────────────────────┐
│ GENERATING, BY THE SYSTEM, QUALITY ASSESSMENT         │      408
│ REPORT DATA FOR THE AUTO-SEGMENTATION COMPRISING      │
│ THE ONE OR MORE MEASURES OF QUALITY                   │
└─────────────────────────────────────────────────────┘
```

FIG. 4

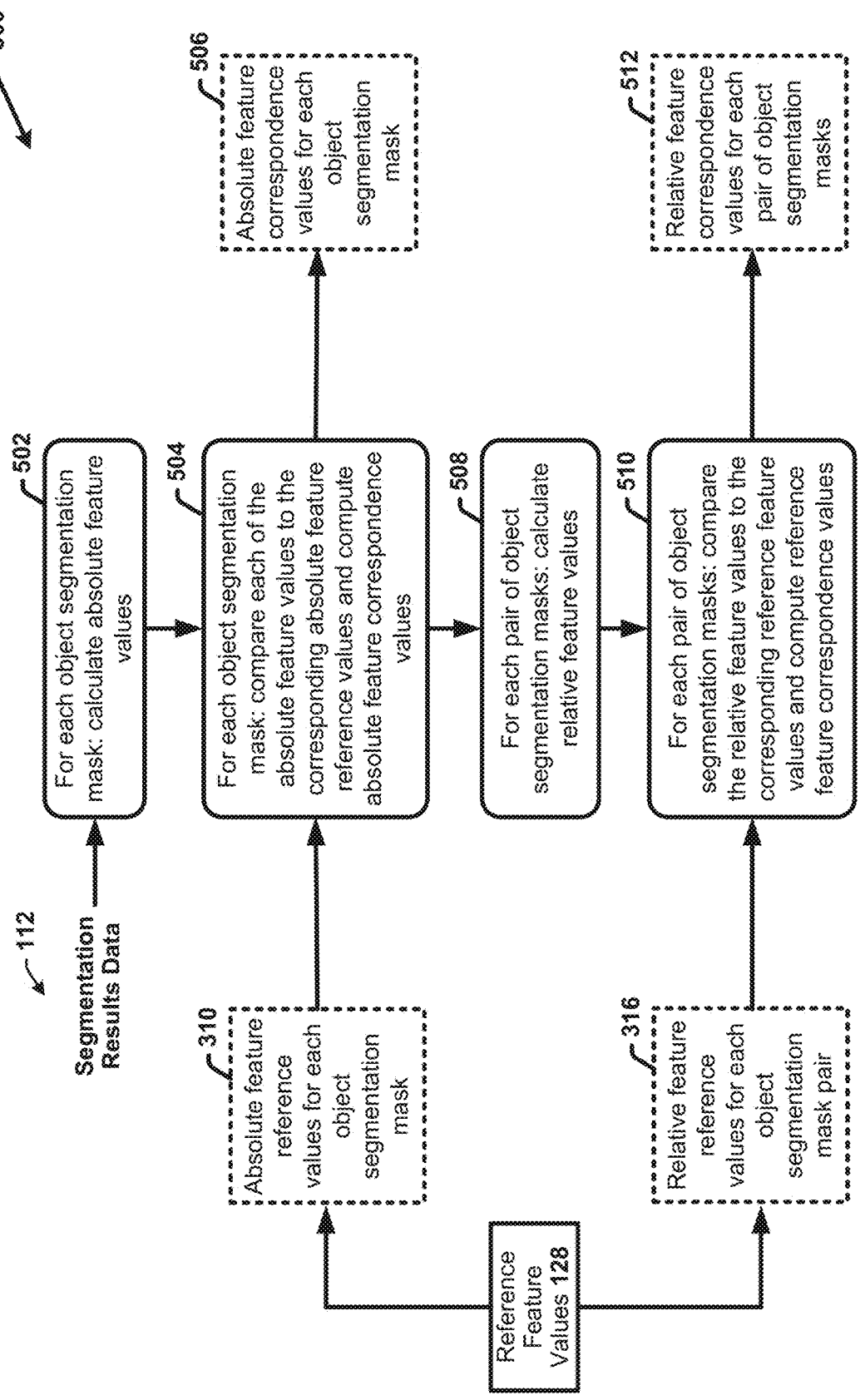

500

112 Segmentation Results Data

502 For each object segmentation mask: calculate absolute feature values

504 For each object segmentation mask: compare each of the absolute feature values to the corresponding absolute feature reference values and compute absolute feature correspondence values 506 Absolute feature correspondence values for each object segmentation mask 310 Absolute feature reference values for each object segmentation mask 508 For each pair of object segmentation masks: calculate relative feature values 510 For each pair of object segmentation masks: compare the relative feature values to the corresponding reference feature values and compute reference feature correspondence values 512 Relative feature correspondence values for each pair of object segmentation masks 316 Relative feature reference values for each object segmentation mask pair Reference Feature Values 128

FIG. 5

Example Auto-Segmentation Quality Results

600

| | Object 1 | Object 2 | Object 3 | Object 4 | Object 5 | Object 6 | Object 8 | # Outliers | Missing | Global Quality |
|---|---|---|---|---|---|---|---|---|---|---|
| Case 1 | 0.88 | 0.56 | 0.9 | 0.66 | 0.67 | 0.86 | 0.18 | 1 | 0 | Acceptable |
| Case 2 | 0.76 | 0.09 | 0.82 | 0.11 | 0.15 | 0.55 | 0 | 3 | 1 | Failed |
| Case 3 | 0.62 | 0.59 | 0 | 0.75 | 0.1 | 0 | 0.05 | 2 | 2 | Failed |
| Case 4 | 0.82 | 0.57 | 0.78 | 0.18 | 0.89 | 0.95 | 0.68 | 1 | 0 | Acceptable |
| Case 5 | 0.67 | 0.78 | 0.86 | 0.95 | 0.72 | 0.82 | 0.65 | 0 | 0 | Acceptable |
| Case 6 | 0.51 | 0.31 | 0.52 | 0.04 | 0.98 | 0.07 | 0 | 2 | 1 | Failed |
| Case 7 | 0.79 | 0.41 | 0.86 | 0.95 | 0.32 | 0.82 | 0.45 | 0 | 0 | Acceptable |
| Case 8 | 0.75 | 0.52 | 0.36 | 0.45 | 0.72 | 0.82 | 0.51 | 0 | 0 | Acceptable |
| Case 9 | 0.88 | 0.78 | 0.86 | 0.95 | 0.28 | 0.82 | 0.65 | 0 | 0 | Acceptable |
| Case 10 | 0.55 | 0.09 | 0.49 | 0.11 | 0 | 0.07 | 0.18 | 4 | 1 | Failed |

FIG. 6

AUTOMATED ORGAN SEGMENTATION OUTPUT QUALITY ASSESSMENT

CROSS-REFERENCE TO RELATED APPLICATIONS

This application is a continuation-in-part of and claims priority to U.S. patent application Ser. No. 17/656,171 filed on Mar. 23, 2022, entitled "SYSTEMS AND METHODS FOR SEGMENTING OBJECTS IN MEDICAL IMAGES." The entirety of the aforementioned application is incorporated by reference herein.

TECHNICAL FIELD

This application relates to medical image processing and more particularly to an automated post-processing tool to assess the quality of deep learning-based organ segmentation in medical images.

BACKGROUND

Radiation therapy is one of the primary modalities for treating cancer in complex anatomical regions such as the head and neck, among others. Owing to the advance in shaping radiation dose for the morphologically complex head and neck anatomy and pathology, intensity-modulated radiation therapy (IMRT) has become the preferred radiotherapy method for head and neck cancer. In inverse optimization, the organs-at-risk (OARs) sparing is achieved by penalizing doses to the correspondingly delineated volumes. Under-segmenting the OARs would expose them to unnecessarily high dose but over-segmenting the OARs could make optimization goals unattainable. Therefore, the effectiveness of IMRT depends on the accuracy of OAR segmentation, which is conventionally manually performed by oncologists and dosimetrists. However, the manual process is not only tedious but also introduces inconsistencies due to both inter-patient and inter-observer variabilities.

To alleviate these problems, automated medical image segmentation has been proposed. In recent years, deep learning-based methods, particularly methods based on the convolutional neural network, have shown great promise in medical image segmentation. Applications include object or lesion classification, organ or lesion detection, organ and lesion segmentation, registration, and other tasks. However, in order to be successfully applied for clinical applications such as IMRT and others, the automated segmentation needs to tackle the inter-patient variability and the large number of anatomical structures in a relatively small area, each presenting specific challenges.

Although deep learning-based segmentation techniques have outperformed statistical shape-appearance based auto segmentation methods, due to inter-patient variability, variance in acquisition protocols/parameters and other factors, the accuracy of deep learning-based segmentation results may be insufficient for clinical applications such as IMRT. Accordingly, techniques for automatically assessing the output accuracy of such segmentation models prior to utilization of the segmentation results for clinical applications are needed.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide an automated post-processing tool to assess the quality of deep learning-based organ segmentation in medical images.

According to an embodiment, a system is provided that comprises a memory that stores computer executable components, and a processor that executes the computer executable components stored in the memory. The computer executable components comprise a feature assessment component that determines current values of defined features of respective organ segmentation masks generated for different organs included in medical image data via auto-segmentation of the medical image data. The computer executable components further comprise a quality assessment component that determines respective measures of correspondence between the current values and the corresponding reference values determined for the defined features and determines one or more measures of quality of the auto-segmentation based on the respective measures of correspondence.

In some embodiments, elements described in the disclosed systems and methods can be embodied in different forms such as a computer-implemented method, a computer program product, or another form.

DESCRIPTION OF THE DRAWINGS

FIG. 4 presents a high-level flow diagram of an example computer-implemented process for automatically assessing the output quality of a multi-organ segmentation model in accordance with one or more embodiments of the disclosed subject matter.

FIG. 5 presents a flow diagram of an example process for determining absolute and relative feature correspondence values in accordance with one or more embodiments of the disclosed subject matter.

FIG. 6 depicts a table illustrating example auto-segmentation quality assessment results in accordance with one or more embodiments of the disclosed subject matter.

DETAILED DESCRIPTION

Figure 1:
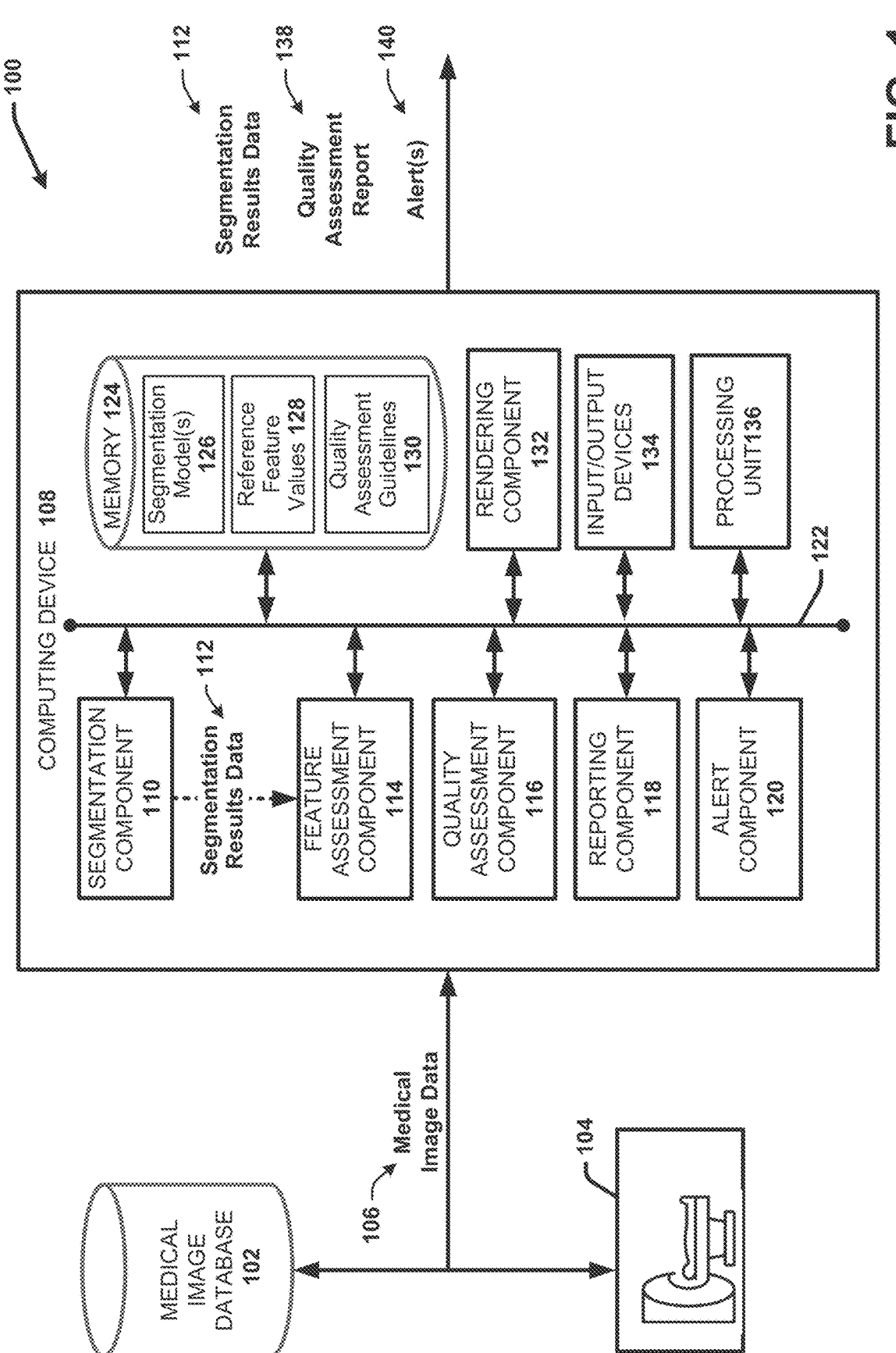
FIG. 1 presents an example system that facilitates automated organ segmentation output quality assessment in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate automatically assessing the output quality of an organ segmentation model. The disclosed techniques were motivated by the usage of deep learning-based auto segmentation of OAR in MR data to guide performance of IMRT. There are many reasons why deep learning multi-organ segmentation in MR may result in inaccurate organ contours. For example, the multi-organ segmentation model may have been trained for a particular MR sequence and may fail when the input is not acquired with the right imaging protocol. As it is very challenging to recognize all variants of an MR sequence, correct segmentation for all variants is not guaranteed. The disclosed techniques provide for automatically detecting and identifying abnormal segmentation results and informing the appropriate entities (e.g., the oncologist, the dosimetrists, etc.) accordingly prior to usage of the results for clinical applications such as IMRT and others.

To facilitate this end, the disclose techniques provide an automated post-processing algorithm to assess the quality of deep-learning-based organ segmentation. The present solution aims at filtering out abnormality in individual auto-segmentations as well as entire cases and therefore prevents exposing inaccurate output to the medical professional. The automated-posted processing algorithm uses the concept of the comparison of a few characteristics of the analyzed segmented structure against expected values obtained in the training process beforehand, approximating the probability of their quality, and aggregating them together. The tool is generalizable and can be extended to additional characteristics as well as various aggregation methods for combining the features together for optimization of different usage scenarios.

The disclosed solution is also modality-independent so, although it was developed for MR segmentations, it can be applied on any other type of medical images. In this regard, the types of medical images processed/analyzed using the techniques described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI or simply MR) images (including T1-weighted images and T2-weighted images), ultrasound (US) images, color flow doppler (CD) images, position emission tomography (PET) images, single-photon emissions computed tomography (SPECT) images, nuclear medicine (NM) images, optical, DWI and the like. The medical images can also include synthetic versions of native medical images such as synthetic X-ray (SXR) images, modified or enhanced versions of native medical images, augmented versions of native medical images, and the like generated using one or more image processing techniques. The types of medical image data processed/analyzed herein can include two-dimensional (2D) image data, three-dimensional image data (3D) (e.g., volumetric representations of anatomical regions of the body), and combinations thereof.

In an example embodiment, a system is provided that comprises a memory that stores computer executable components, and a processor that executes the computer executable components stored in the memory. The computer executable components comprise a feature assessment component that determines current values of defined features of respective segmentation masks generated for different anatomical structures included in medical image data via auto-segmentation of the medical image data. The computer executable components further comprise a quality assessment component that determines respective measures of correspondence between the current values and the corresponding reference values determined for the defined features and determines one or more measures of quality of the auto-segmentation based on the respective measures of correspondence. The computer executable components further comprise a reporting component that generates quality assessment report data for the auto-segmentation comprising the one or more measures of quality. In various embodiments, the one or more measures of quality comprise a quality measure for a specific structure or structure set represented by a segmentation mask or group of the organ segmentation masks, and wherein the reporting component integrates the quality measure with the specific structure or structure set in a standard clinical data format, such as the Digital Imaging and Communications in Medicine (DICOM) format. or another standard clinical reporting format.

In some implementations, the one or more measures of quality comprise a structure-specific quality measure for each of the respective segmentation masks that reflects a measure of quality of each of the respective segmentation masks. In some aspects, the quality assessment component determines the structure-specific quality measure for each of the respective segmentation masks based on aggregated correspondence values for a plurality of the defined features associated with each of the respective segmentation masks. The one or more measures of quality may further comprise an overall measure of quality of the auto-segmentation determined by the assessment component based on aggregation of each of the organ-specific quality measures.

In various embodiments, the defined features comprise absolute features representing independent characteristics of the respective organ segmentation masks and relative features representing relative characteristics of different pairs of the respective organ segmentation masks. For example, the absolute features can comprise one or more geometrical features related to the size or shape of the respective organ segmentation masks (e.g., volume, surface area, centroid coordinates, etc.). The absolute features may further comprise latent features that are extracted from the segmentation output using machine-learning methods (PCA, neural networks, etc.) which and are not necessary meaningful for human observer, but can be used to characterize the correctness of a segmentation output. The relative features may comprise relative distances between each segmentation mask (e.g., respective mask centroid coordinates) included in the different pairs. In various embodiment, the corresponding reference values for the defined features (e.g., the absolute features and the relative features) are based on ground truth organ segmentation data for the different organs as depicted in training medical image data used to train respective organ segmentation models used to perform the auto-segmentation. In some implementation, the feature assessment component determines the corresponding reference values for the defined features based on analysis of the ground truth organ segmentation data.

In one or more embodiments, the reporting component can store the quality assessment report data with segmentation data for the medical image data in one or more medical image datastores, the segmentation data comprising the respective segmentation masks. The computer-executable components can also include a rendering component that presents the respective segmentation masks and the quality assessment report data via a device display associated with one or more clinical entities in association with employing the respective organ segmentation masks to facilitate a clinical procedure on a patient from which the medical image data was captured. The computer-executable components can further comprise an alert component that generates an alert data based on the one or more measures of quality failing to satisfy a threshold quality measure and provides the alert data to one or more devices associated with one or more clinicians. For example, the alert data can relate to a specific structure or structure set represented by a segmentation mask or group of the segmentation masks, and wherein the alert component integrates the alert data with the specific structure or structure set in a standard clinical data format. In this regard, the alert data can be provided to the end user without introducing any change in the current clinical workflow (e.g., reading an additional report about output quality). This can be solved by including keywords (such as "error," "warning," "empty," etc.) in structure name, or structure-set name, or series-description of the structure-set, which are standard DICOM tags and displayed in any radiation therapy (RT) planning software by default.

In some embodiments, the computer-executable components further comprise a recommendation component that determines one or more clinical workflow actions to be performed based on the one or more measure of quality failing to satisfy a threshold quality measure and provides recommendation data identifying the one or more clinical workflow actions to one or more devices associated with one or more clinicians.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates automated organ segmentation output quality assessment in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a computing device 108 that include several computer executable components, including segmentation component 110, feature assessment component 114, quality assessment component 116, reporting component 118, alert component 120, and rendering component 132. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 124 of the computing device 108 which can be coupled to processing unit 136 for execution thereof. Examples of said and memory and processor (or processing unit) as well as other suitable computer or computing-based elements, can be found with reference to FIG. 10, and can be used in connection with implementing one or more of the systems or components shown and described in connection with FIG. 1 or other figures disclosed herein. Memory 118 can further store a variety of information that is received by, used by, and/or generated by the computing device 108 in association with assessing the quality auto-segmented medical image data. In the embodiment shown, this information includes (but is not limited to), segmentation models 126, reference feature values 128 and quality assessment guidelines 130.

System 100 further includes a medical image database 102 and a medical imaging system 104. The medical image database 102 can correspond to any suitable database that stores medical image data 106 for processing by the computing device 108, such as medical image database associated with a picture archiving and communication system (PACS) or the like. The medical imaging system 104 can correspond to any medical imaging system capable of capturing and generating (e.g., via medical image reconstruction processing technology) medical image data 106 for processing by the computing device 108. The medical image data 106 can include any type of medical image data capable of being automatically segmented via one or more segmentation models 126, including medical image data acquired via any medical imaging modality (e.g., (e.g., MR, CT, PET, SPECT, US, XR, etc.) and depicting any anatomical region of the body.

In this regard, in accordance with system 100, the computing device 108 can receive medical image data 106 provided by the medical image database 102 and/or the medical imaging system 104 and processes the medical image data 106 via one or more segmentation models 126 (e.g., using segmentation component 110) to generate segmentation results data 112. Additionally, or alternatively, the computing device 108 can receive the segmentation results data 112 as generated by another system/device via application of one or more segmentation models 126 to the medical image data 106.

The segmentation results data 112 can include information that defines the boundary or contour of one or more defined anatomical objects depicted in the medical image data 106 in 2D and/or 3D (depending on the type of image from which its segmented) relative to the original image data from which it was segmented. For example, the segmentation results data 112 can comprise one or more segmentation masks generated for one or more anatomical objects, image mark-up data including boundary lines, points, circles, etc.

of the anatomical objects, and/or image data of the anatomical objects as extracted from the input image. The segmentation results data 112 can further include the original medical image data from which the corresponding segmentations were generated. The one or more anatomical objects can include any anatomical object that has consistent or substantially consistent geometrical properties across all patients or a defined patient subgroup (e.g., grouped by age or another demographic factor), such as organs as opposed to lesions. The anatomical objects are not limited to organs however and can include any defined anatomical object or feature. It should be appreciated that the number and type of anatomical objects segmented can vary depending on the input image data type, the anatomy depicted and the particular anatomical objects which the one or more segmentation models 126 are configured to segment. In various embodiments, the one or more segmentation models 126 can correspond to a multi-organ segmentation model configured to segment a plurality of different organs (and/or other types of anatomical objects) depicted in the medical image data 106. The number of different anatomical objects segmented for the medical image data 106 can vary. For example, in some implementations in which the medical image data 106 comprises MR head and neck scan data for a patient, the one or more segmentation models 126 can correspond to a multi-organ segmentation model that segments up to about 30 different defined anatomical structures included in the MR head and neck scan data. However, the disclosed techniques can also be applied to evaluate segmentation results that include only a single segmented anatomical object.

Figure 2:
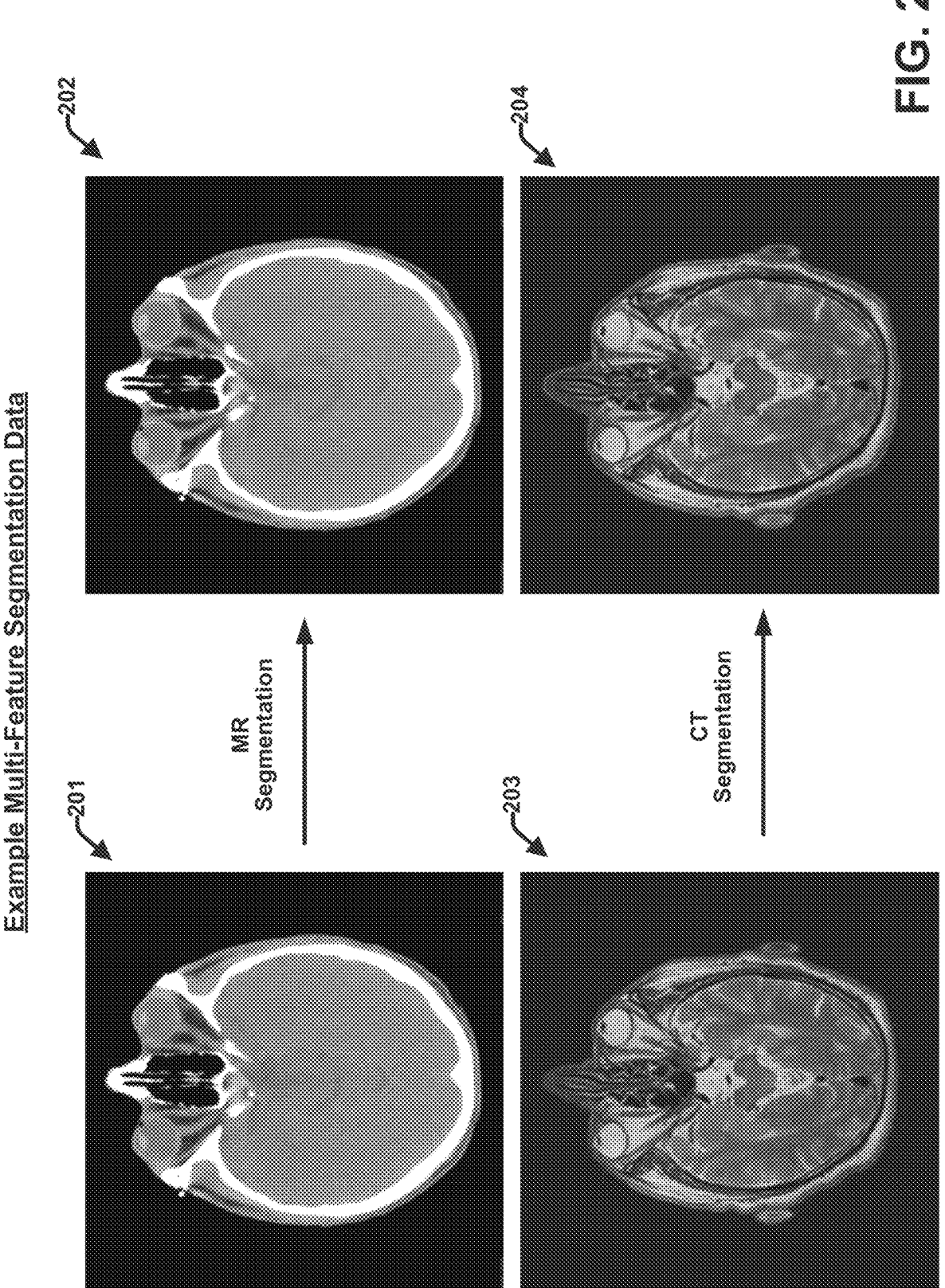
FIG. 2 illustrates example multi-organ segmentation of magnetic resonance (MR) image data and computed tomography (CT) image data in accordance with one or more embodiments of the disclosed subject matter in accordance with one or more embodiments of the disclosed subject matter.

FIG. 2 illustrates example multi-organ segmentation of magnetic resonance (MR) image data and computed tomography (CT) image data in accordance with one or more embodiments of the disclosed subject matter in accordance with one or more embodiments of the disclosed subject matter. In the example shown in FIG. 2 the multi-organ segmentation data includes MR segmentation data 202 generated from MR image data 201 corresponding to an MR brain scan of a patient. The multi-organ segmentation data further includes CT segmentation data 204 generated from CT image data 203 corresponding to a CT brain scan of a patient. The MR segmentation data 202 provides segmentation data in the form of segmentation boundary marks or contours around various defined anatomical objects (e.g., tissues, vessels, regions of interest (ROIs), etc.) depicted in the MR image data 201. The CT segmentation data 204 provides segmentation data in the form of segmentation masks generated over the eyeball and the optic nerves as depicted in the CT image data 203. The MR segmentation data 202 and the CT segmentation data 204 correspond to two example illustrations of segmentation results data 112. It should be appreciated that the segmentation data segmentation data depicted in FIG. 2 is merely exemplary and a variety of different types of segmentation data results for a variety of different anatomical objects associated with all regions of the body are envisioned.

With reference again to FIG. 1, in accordance with the disclosed techniques, the segmentation results dataset 112 corresponds to anatomical object image segmentations (e.g., such as those depicted in FIG. 2) as segmented from the respective original 2D and/or 3D medical images (e.g., included in the medical image data 106) by the segmentation component 110 using one or more segmentation models 126. As noted above, the specific anatomical objects or segmented can vary depending on the type of the medical image data (e.g., modality and scanned anatomical region) and the specific objects that the one or more segmentation models 126 are configured to segment. Regardless of the type of the medical image data 106, the specific anatomical objects (or object) segmented therefrom via the one or more segmentation models 126 include predefined anatomical objects. The specific predefined anatomical objects correspond to the specific anatomical objects that the one or more segmentation models 126 are configured to segment. In particular, the one or more segmentation models 126 can comprise deep-learning anatomical object segmentation models trained to segment one or more defined anatomical objects from a particular type of medical image data 106 (e.g., modality and anatomical region). As applied to several embodiments, the one or more segmentation models 126 correspond to a multi-organ segmentation model trained to segment a plurality of different defined anatomical objects depicted in the medical image data 106. In accordance with deep-learning segmentation model training, the multi-organ segmentation model was trained using a supervised machine learning process on a training dataset comprising ground-truth data defining the correct segmentations for corresponding input medical image data. For example, the ground-truth data typically comprises manually applied mark-ups defining the boundary contours of the respective anatomical organs (or other defined anatomical objects) to be segmented.

The disclosed techniques utilize this ground-truth segmentation data to define expected characteristics of each anatomical object to be segmented by the corresponding segmentation model. For example, as applied to multi-organ segmentation of medical image data the expected characteristics can include expected 2D and/or 3D geometrical properties (e.g., size, shape, surface area, volume) of each organ segmentation of the multiple organs to be segmented. In this regard, using the ground-truth (GT) segmentation data for each organ/object as applied to a plurality of different medical images corresponding to different patients included the training data, the disclosed techniques define, for each organ or object segmentation, one or more features (e.g., geometrical properties, such as volume, surface area, etc.) and expected values of the features (e.g., average volume observed in the GT examples for the organ/object, average surface area observed in the GT examples for the organ/object, etc.). This information is represented in system 100 as reference feature values 128. Once the features and expected values of the features for each object segmentation have been defined in the reference feature values 128 and the corresponding segmentation model has been trained, the segmentation component 110 can apply the segmentation model to new medical image data (e.g., medical image data 106) to generate segmentation results data 112 comprising the automated segmentation model generated segmentations for the respective defined anatomical objects/organs. The feature assessment component 114 further determines the current values of the defined features of the respective organ/object segmentations (e.g., segmentation masks and/or information defining the boundary contours of the respective anatomical objects/organs) included in the segmentation results data 112.

The quality assessment component 116 further determines respective measures of correspondence between the current values and the corresponding reference values determined for the defined features as provided in the reference feature values 128, (e.g., a measure of correspondence between current volume of a segmented organ and the expected volume of the segmented organ) and determines one or more measures of quality of the auto-segmentation based on the respective measures of correspondence (e.g., whether the organ segmentation is accurate because the current volume corresponds to the expected volume) and predefined threshold criteria regarding acceptable (e.g., corresponding to correct/accurate segmentations) and unacceptable (e.g., corresponding to incorrect/inaccurate segmentations) measures of correspondence (e.g., as provided in the quality assessment guidelines 130).

In some implementations, the one or more measures of quality comprise an organ-specific quality measure for each of the respective organ segmentation masks that reflects a measure of quality of each of the respective organ segmentation masks. In some aspects, the quality assessment component 116 determines the organ-specific quality measure for each of the respective organ segmentation masks based on aggregated correspondence values for a plurality of the defined features associated with each of the respective organ segmentation masks. The one or more measures of quality may further comprise an overall measure of quality of the auto-segmentation determined by the quality assessment component based on aggregation of each of the organ-specific quality measures.

In this regard, as described in greater detail below, the quality assessment component 116 can assess the quality of the auto-segmentation (i.e., the segmentation results data 112) on an individual organ or object level, providing one or more measures of the quality (e.g., degree of accuracy or correctness) of each organ/object included in the segmentation results data 112 (e.g., assuming a multi-organ/object segmentation model). For each organ/object segmented the quality assessment can be based on a plurality of different defined features, including absolute features and relative features, as described in greater detail below. The quality assessment component 116 can also assess the overall quality of the auto-segmentation based on the aggregated measures of quality of the individual organs/objects using various aggregation algorithms as tailored to different use cases.

The reporting component 118 can further generate a quality assessment report (e.g., quality assessment report 138) for the auto-segmentation comprising results of the quality assessment performed by the quality assessment component 116. The rendering component 132 can further present the segmentation results data 112 (e.g., comprising the respective organ segmentation masks/data such as that illustrated in FIG. 2) and the quality assessment report 138 via a device display (e.g., included in input/output devices 134) associated with one or more clinical entities in association with employing the segmentation results data 112 to facilitate a clinical procedure on a patient from which the medical image data 106 was captured. The reporting component 118 can also store the quality assessment report 138 with the segmentation results data 112 for the medical image data 106 in one or more medical image data stores (e.g., medical image database 102 and/or memory 124). In some embodiments, the alert component 120 can also generate an alert data (e.g., alerts 140) based on the one or more measures of quality of the auto-segmentation failing to satisfy a threshold quality measure (e.g., as defined in the quality assessment guidelines 130) and provide the alert data to one or more devices associated with one or more clinicians. For example, the alert component 120 can generate alert data in the form of standard DICOM tags integrated on or within respective structures or structure sets represented by the corresponding segmentation masks. The alert tags can indicate the measure of quality of the respective structures or structure sets. For example, the alert tags can indicate if a particular structure's segmentation is accurate or inaccurate and thus associated with a "warning" keyword.

In this regard, any information received by (e.g., medical image data 106 and/or segmentation results data 112 in some implementations) and/or generated by (e.g., segmentation results data 112, quality assessment report 138, alerts 140, etc.) by the computing device 108 can be presented or rendered to a user via a suitable display. The display can be included with the computing device 108 (e.g., via input/output devices 134) and/or another user device (not shown) that can be communicatively and operatively coupled (e.g., vie one or more wired or wireless communication connections) to the computing device 108. In this regard, the computing device 108 can correspond to any suitable computing device employed by a user (e.g., a clinician, a radiologist, a technician, a machine learning (ML) model developer, or the like) to review medical image data, segmentation results data 112 and the corresponding quality assessment report 138 for the segmentation results data 112 in association with utilizing the segmentation result data to facilitate a clinical procedure for a patient (e.g., IMRT or another clinical procedure). For example, in various embodiments, one or more of the components of the computing device 108 can be associated with a medical imaging application that facilitates accessing and reviewing medical images via an interactive graphical user interface (GUI) displayed at the computing device, generating and reviewing anatomical object segmentations for the medical images via the GUI, annotating the medical images, running inferencing models on the medical images and the like. In some implementations of these embodiments, the computing device 108 can correspond to an application server that provides at least some of these features and functionalities to user devices (e.g., not shown) via a network accessible platform, such as a web-application or the like. With these embodiments, the computing device 108 can be communicatively coupled to respective user devices (e.g., clinician devices) via one or more wired or wireless communication networks (e.g., the Internet) and the respective user devices can access one or more of the features and functionalities of the computing device 108 as a web-application using a suitable web browser. Additionally, or alternatively, system 100 can employ a local deployment architecture (as depicted in system 100). Various other deployment architectures for system 100 and other systems described herein are envisioned.

In this regard, the computing device 108 can include one or more input/output devices 134 (e.g., a keyboard, a mouse, a touchscreen, a display, etc.) that provide for receiving user input in association with usage of the feature and functionalities of the computing device 108 and presenting segmentation results data 112, quality assessment reports 138 and alerts to users. Examples of some suitable input/output devices 134 are described with reference to FIG. 10 with respect to input devices 1028 and output device 1036). The computing device 108 can further include a device bus 122 that communicatively couples the respective elements/components of the computing device to one another.

Figure 3:
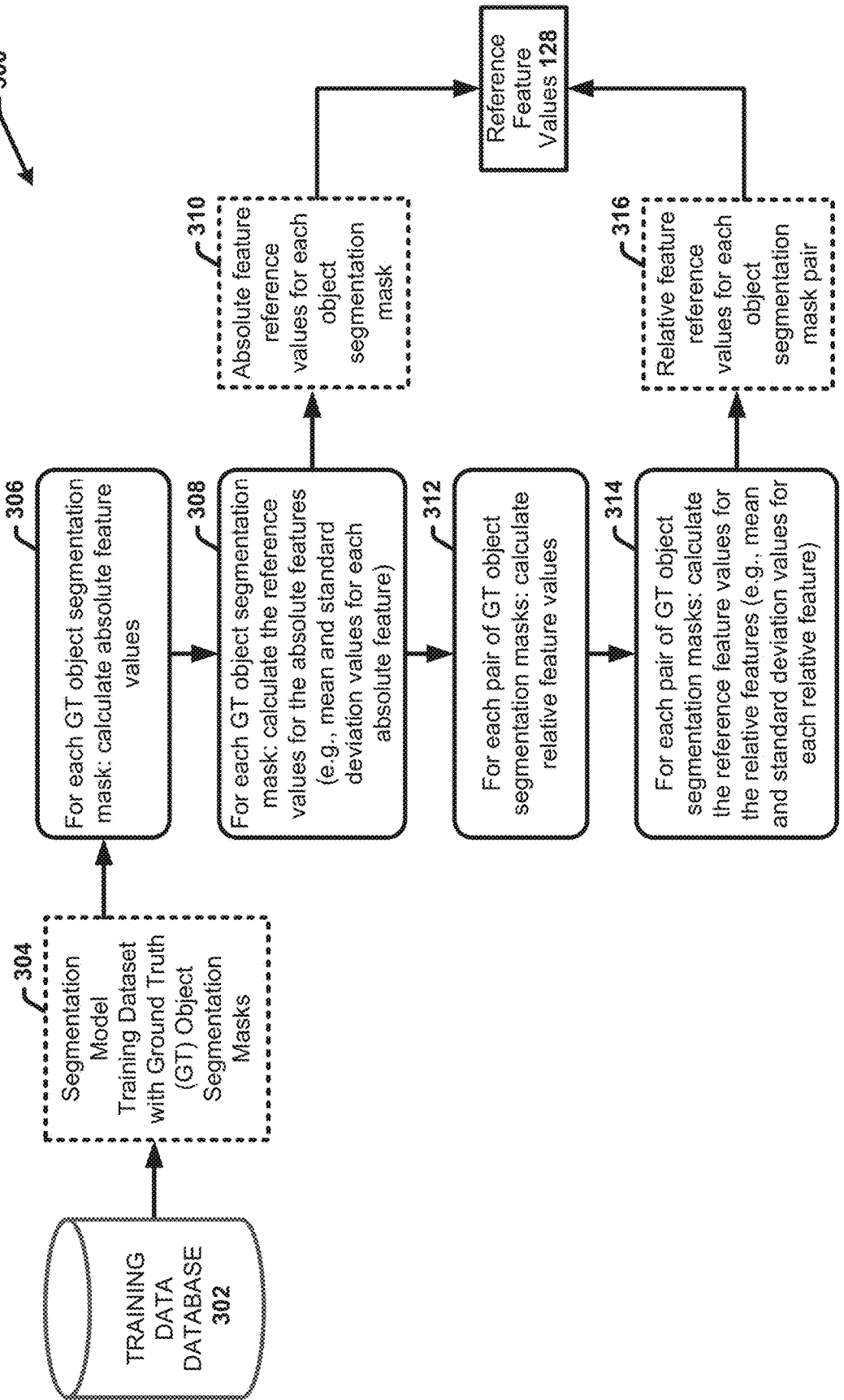
FIG. 3 presents a high-level flow diagram of an example process for determining reference feature values for a multi-organ segmentation model in accordance with one or more embodiments of the disclosed subject matter.

FIG. 3 presents a high-level flow diagram of an example process 300 for determining reference feature values for a multi-organ segmentation model in accordance with one or more embodiments of the disclosed subject matter. With reference to FIGS. 1-3, process 300 corresponds to an example process that can be performed by the feature assessment component 114 to define the reference feature values 128 for a particular segmentation model 126. Throughout several example embodiments, the disclosed techniques are described wherein the segmentation model 126 corresponds to a multi-organ/object segmentation model trained to segment a plurality of different anatomical organs/objects included in the input medical image data. However, it should be appreciated that the disclosed techniques can be applied to individual organ/object segmentation models.

As noted above, the reference feature values 128 can be determined by the feature assessment component 114 based on the GT segmentation data associated with the training medical images used to train the segmentation model 126. In the embodiment shown in FIG. 3, this GT segmentation data can be included with the training medical images (i.e., the training dataset) in training data database 302. In this regard, in accordance with process 300, at 304, the feature assessment component 114 can access the segmentation model training data set with the GT object segmentation masks applied to the respective organs/objects that the model was trained to segment. For instance, assuming the segmentation model comprises a multi-organ segment OAR in head and neck MR data, the respective organs/objects may include but are not limited to: the anterior segment of the eyeball, the posterior segment of the eyeball, the lacrimal gland, the parotid glands, the submandibular glands, the extended oral cavity, the buccal mucosa, the lips, the mandible, the cochlea, the pharyngeal constrictor muscles, the thyroid gland, the brain, the brainstem, the pituitary gland, the optic chiasm, the optic nerve, the spinal cord, the carotid arteries, and others. In this regard, the segmentation model training dataset includes a plurality of input medical images (e.g., captured from different patients/subjects) of the same type (e.g., modality and scanned/imaged anatomical ROI) with GT object/organ segmentation data for the respective anatomical objects/organs 1-N (e.g., wherein N can include any integer greater than 1) that the segmentation model was trained to segment. The GT object/organ segmentation data can include segmentation mask data (or simply segmentation masks) that defines the boundary contours of the respective objects/organs.

At 306, for each GT object segmentation mask (for each of the different anatomical objects/organs segmented) the feature assessment component 114 calculates the absolute feature values. In this regard, as noted above, the defined features for each object/organ segmentation can include absolute features and relative features. The absolute features represent independent characteristics of the respective organ segmentation masks such as geometrical features related to the size or shape of the respective organ segmentation masks. Some example absolute features include can include but are not limited to: object/organ volume (e.g., a number of voxels in the entire organ contour), organ/object surface area (e.g., number of voxels in the entire organ contour's surface), and organ/object centroid coordinates (e.g., x, y, z). The absolute features can also include one or more latent features extracted from the segmentation image data input as well, such as the intensity within a particular anatomical structure. For example, absolute features can include the output of any machine-learning method that can reduce the information content of the input images to a lower dimensional representation such as PCM (principal component analysis) or a CNN-based (convolutional neural network) encoder network. It should be appreciated that various other geomaterial properties may defined as absolute features and that the absolute features can vary depending on whether the segmentation medical image data comprises 3D or 2D image data. The number of absolute features calculated and defined for each segmented anatomical object/organ can vary. For example, in some implementations, for each anatomical object/organ, the absolute features can include a single feature (e.g., volume). In other implementation, the absolute features can include a plurality of different features (e.g., volume, surface area, centroid coordinates, and other absolute features). In this regard, at 306, for each different GT organ/object segmentation mask, and each absolute feature evaluated, the feature assessment component 114 can calculate the distribution of the values observed.

At 308, for each different GT organ/object segmentation mask, the feature assessment component 114 can further calculate the reference values for each absolute feature, such as the means and/or standard deviation (STD) values for each absolute feature. For example, assuming one absolute feature includes the volume of an object/organ segmented (e.g., the brain for instance), at 308 the feature assessment component 114 can calculate the mean and the STD of the observed volume values of the object/organ segmented based on the distribution of values calculated for each of the corresponding GT segmentation masks. In this regard, as a result of steps 306 and 308, at 310 the feature assessment component 114 generates the absolute feature (AF) reference values for each object segmentation mask (e.g., Object 1 (e.g., brain): AF1 (e.g., volume), reference values=(mean observed volume, STD observed volume, AF2 (e.g., surface area), reference values=(mean observed volume, STD observed volume); (Object 2 (e.g., brainstem): AF1 (e.g., volume), reference values=(mean observed volume, STD observed volume, AF2 (e.g., surface area), reference values= (mean observed volume, STD observed volume); and so on for each object 1-n and each AF defined for each object).

At 312, the feature assessment component 114 can further calculate the distribution of observed relative feature values. The relative features represent relative characteristics of different pairs of the respective organ segmentation masks, such as relative distances between each organ segmentation mask included in the different pairs (e.g., the distance between two organs using the centroid coordinates). In this regard, at 312, the feature assessment component 114 can define different pairs of the GT segmentation masks. The number and distribution of the different pairs can be predefined and encompass all possible pair combinations or a relevant defined subset thereof. For each pair of GT object segmentation masks, the feature assessment component 114 can calculate the distribution of observed distances between the respective mask centroid coordinates and/or other relative features (e.g., relative positions of boundary lines, relative orientations, etc.). At 314, for each pair of GT object segmentation masks the feature assessment component 114 can further calculate the reference feature values for the relative features, such as the mean and standard deviation values of each relative feature. For example, assuming a pair of object/organs includes the brainstem and the eyeball, the relative features can include the distance between the respective organ centroid coordinates, the reference value for this relative feature can include the mean observed distance value and/or the STD of the observed distance values calculated at 312. In this regard, as a result of steps 312 and 314, at 316 the feature assessment component 114 generates the relative feature (RF) reference values for each object segmentation mask pair. The absolute feature reference values and the relative feature reference values calculated generated at 310 and 316 constitute the reference feature values 128 for assessing the output quality of the segmentation results of the segmentation model at runtime (e.g., after model training and deployment in the clinical workflow).

FIG. 4 presents a high-level flow diagram of an example computer-implemented process 400 for automatically assessing the output quality of a multi-organ segmentation model in accordance with one or more embodiments of the disclosed subject matter. Process 400 presents a high-level method for evaluating the output quality of the segmentation results of the segmentation model for which the reference feature values were defined in accordance with process 300 (e.g., based on the GT segmentation data used for the model training).

With reference to FIGS. 1-4, in accordance with process 400, at 402, process 400 comprises determining, by a system comprising a processor (e.g., system 100 and additional systems described herein), current values of defined features (e.g., one or more absolute features and/or relative features) of respective segmentation masks (e.g., included in segmentation results data 112) generated for different anatomical structures (e.g., and/or other defined anatomical organs and other objects/structures) included in medical image (e.g., medical image data 106) data via auto-segmentation of the medical image data (e.g., via segmentation component 110 using one or more segmentation models 126). At 404, method 400 comprises determining, by the system (e.g., via quality assessment component 116), respective measures of correspondence between the current values and corresponding reference values determined for the defined features (e.g., as determined in accordance with process 300 and provided in the reference feature values 128). At 406, method 400 further comprises determining, by the system, one or more measures of quality of the auto-segmentation based on the respective measures of correspondence (via quality assessment component 116). At 408, method 400 further comprises generating, by the system, quality assessment report data (e.g., quality assessment report 138) for the auto-segmentation comprising the one or more measures of quality. For example, the quality assessment report data can comprise quality information integrated on or withing the segmentation results (e.g., the segmentation masks directly and/or as metadata) that is capable of being rendered with the segmentation results by a clinical reporting tool. For instance, the quality information may be integrated with the segmentation results as metadata tags in a standard clinical format (e.g., DICOM, RTSS or the like). In some embodiments, quality information can identify or indicate the name of a structure or structure set represented by a particular segmentation mask or group of segmentation masks and provide a measure of quality of the structure or structure set.

FIG. 5 presents a flow diagram of an example process 500 for determining absolute and relative feature correspondence values in accordance with one or more embodiments of the disclosed subject matter. With reference to FIGS. 1-5, process 500 provides additional details regarding the quality assessment component 116 and steps 402 and 404 of process 400. In this regard, in one or more embodiments, at 502, the feature assessment component 114 can analyze the segmentation results data 112 and calculate the current absolute feature values for each object segmentation mask. For example, the feature assessment component 114 can identify the absolute features defined for each object segmentation mask as provided in the reference feature values 128 (e.g., volume, surface area, centroid coordinates, etc.) and calculate the corresponding current absolute feature values. At 504, for each object segmentation mask, the quality assessment component 116 can compare each of the absolute feature values (or value if only a single absolute feature is defined) calculated at 502 with the corresponding absolute feature reference values (e.g., corresponding to 310) and compute the absolute feature correspondence values, resulting in absolute feature correspondence values for each object segmentation mask 506. In this regard, for each organ/object segmentation mask, the absolute feature correspondence values represent a measure of the degree of correspondence (or deviation) between the current value for each absolute feature and the reference value for the corresponding absolute feature. For example, assuming the absolute features for each organ segmentation mask include volume and surface area, the absolute feature correspondence values can include a first correspondence value that reflects the degree of correspondence (or deviation) between the current volume value and the reference mean volume value for the particular organ segmentation mask, and a second correspondence value that reflects the degree of correspondence (or deviation) between the current volume value and the reference mean volume value for the particular organ segmentation mask. It should be appreciated that various statistical metrics may be used to represent the correspondence values based on comparison of the current feature values to the reference feature values.

At 508, for each pair of object segmentation masks defined in the reference data for the segmentation model, the feature assessment component 114 can further calculate the relative feature values based on the segmentation results data 112. For example, in implementations in which the relative features encompass the respective distances between centroid coordinates of respective organ/object segmentation masks, at 508 the feature assessment component can compute the respective distance values. In this regard, assuming the reference feature values 128 represent all pair combinations, each organ/object segmentation mask will have a set of current distance values that represent the respective distances of the centroid coordinates of a given organ/object segmentation mask to each of the centroid coordinates of all other organ/object segmentation mask. For instance, for a given mask A, the set will include distance between mask A and mask B, distance between mask A and mask C, distance between mask A and mask D, distance between mask A and mask E . . . and so on. At 510, for each pair, the quality assessment component 116 can further compare the relative feature values to the corresponding reference feature values and compute the reference feature correspondence values, resulting in relative feature correspondence values for each object segmentation mask pair 512 (or a single relative feature correspondence value if only a single relative feature, such as distance, is used). For instance, in some implementations, the feature correspondence values for all current mask distances associated with mask A may include a set of correspondence values that that represent the degree of correspondence (or deviation) between the current distance values and the corresponding reference distance values (e.g., difference between the current mask A to mask B distance and the reference mean mask A to mask B distance, difference between the current mask A to mask C distance and the reference mean mask A to mask C distance, difference between the current mask A to mask D distance and the reference mean mask A to mask D distance . . . and so on).

With reference to FIGS. 1 and 5, as a result of process 500, the quality assessment component 116 can generate a subset of correspondence values for each object/organ segmentation mask that respectively reflect measures of correspondence between the current feature values of a given organ/object segmentation mask and the reference feature values for the given organ/object segmentation mask. In some embodiments, the quality assessment component 116 can determine one or more measure of quality of each organ/object segmentation mask based on the aggregated subset of correspondence vales associated therewith and predefined quality threshold criteria defined in the quality assessment guidelines 130. For example, the quality assessment component 116 can generate an aggregated correspondence score for each organ/object segmentation mask that represents an aggregated combination of each of the feature correspondence values in the corresponding subset. The aggregated correspondence score corresponds to an overall measure of quality of the organ/object segmentation based on all of the assessed features for that organ/object segmentation. The quality assessment component 116 can further determine whether the quality of a given organ/object segmentation is acceptable (e.g., meaning the segmentation is sufficiently accurate) based on whether the aggregated correspondence score is greater than a minimum threshold correspondence score defined in the quality assessment guidelines 130. In some implementations, the quality assessment component 116 can characterize any organ/object segmentation that does not satisfy the threshold correspondence score as an "outlier" segmentation.

In some embodiments, the quality assessment component 116 can further assess the overall quality of the segmentation results data 112 as a function of the number of outlier segmentations and/or the combined aggregated correspondence scores for all of the segmentation masks represented in the segmentation results data 112. For example, in some implementations, the quality assessment component 116 can generate a mean correspondence score for the segmentation results data 112 based on the combined aggregated correspondence scores for all of the segmentation masks represented in the segmentation results data 112. The quality assessment component 116 can further determine whether the overall quality of segmentation results data 112 is acceptable based on whether the mean aggregated correspondence score is greater than a minimum overall threshold correspondence score defined in the quality assessment guidelines 130. In another example, the quality assessment component 116 can determine whether the overall quality of segmentation results data 112 is acceptable or not based on whether the number of outliers is less than or equal to a maximum number of outliers defined for the segmentation model in the quality assessment guidelines data 130.

It should be appreciated that the quality assessment component 116 can employ various additional or alternative statistical analysis algorithms to assess the degree of correspondence between the current absolute and/or relative feature values associated with each organ segmentation mask and the corresponding reference feature values (e.g., which may include mean and/or STD values). The quality assessment component 116 can also employ various aggregation techniques to aggregate the set of current absolute and/or relative feature values associated with each organ segmentation mask in association with comparing the set to the corresponding reference feature values to determine measures of correspondence (or deviation) between the current feature values and the reference feature values for each organ/object segmentation mask and/or to determine measures or quality of the individual organ segmentation masks and/or the overall quality of the segmentation results data 112.

For example, in some embodiments, the quality assessment component 116 can assess quality of the segmentation results data 112 using one or more probability values that reflect a measure of accuracy of the segmentation results data 112 as a function of the degree of correspondence (or deviation) between that current feature values and the corresponding reference feature values. In this regard, in an example embodiment, assume the segmentation model applied to generate the segmentation results data 112 segments 3D medical image data (e.g., MR data, CT data, etc.) and defines the geometrical contours of a plurality of different anatomical objects/organs (e.g., a multi-organ/object segmentation model). For each organ/object, assume the absolute features defined in the reference feature values, include volume and surface area and the relative features include distances between the centroid coordinates for all respective pair combinations of the of organs/object segmentations. In accordance with this example embodiment, for each feature (e.g., volume, surface area, and every distance between two organ's centroids), the quality assessment component 116 can approximate the probability of the auto-segmentation being correct using univariate Gaussian normal distribution in accordance with Equation 1 below, wherein $\mu$ represents the feature's reference mean value, $\sigma$ represents the feature's reference STD value (both calculated based on the training dataset), y represents the feature probability value, and x represents the measured current feature value based on the segmentation results data 112.

$$y = \frac{1}{\sigma\sqrt{2\pi}} e^{-\frac{(x-\mu)^2}{2\sigma^2}}. \qquad \text{Equation 1}$$

As volume and surface area's probability values are single numbers, there is an entire vector of values for the Euclidean distances between organ's centroid. Therefore, the quality assessment component 116 can calculate the mean value out of this vector to obtain also a single number for the Euclidean distance feature probability in accordance with Equation 2:

$$y_{RED} = \frac{\sum_{i=1}^{n-1} y_{IRED_i}}{n}, \qquad \text{Equation 2}$$

where: $Y_{RED}$ represents an overall Euclidean distance feature probability and $Y_{IRED}$ corresponds to a vector of individual relative Euclidean distances feature probabilities (i.e., an approximated probability of the correctness of the distance between a chiasma contour's centroid to all the other organ contours' centroids).

For each organ/object segmentation (i.e., contour), the quality assessment component 116 can aggregate all the individual features' probabilities using an aggregation function such as the average of probabilities, in accordance with Equation 3:

$$Y = \frac{y_{AV} + y_{AS} + y_{RED}}{3}, \qquad \text{Equation 3}$$

where: Y is the final approximated probability, $Y_{AV}$ is an absolute volume feature probability, and $Y_{AS}$ is the absolute surface area feature probability, and $Y_{RED}$ is the overall relative Euclidean distance feature probability. In accordance with this example, Y corresponds to a finally probability value for a given organ/object segmentation that reflects the probability that the segmentation is accurate. In this regard, Y value can be or correspond to a quality measure for the corresponding organ segmentation.

The quality assessment component 116 can further assess the quality of the segmentation results data 112 as a function of the respective final approximated probability values (i.e., the Y's for each organ/object segmentation) and predefined criteria regarding acceptable and unacceptable final approximated probability values (e.g., one or more defined thresholds provided in the quality assessment guidelines data 130). For example, the quality assessment component 116 can assess the quality of the auto-segmentation segmentation results data 112 on two levels, the individual level for each organ/object segmentation and the overall or global level. As applied to the individual organ/object segmentation level, in some implementations, the quality assessment component 116 can determine that an individual organ/object segmentation is correct (i.e., accurate) and "acceptable" if the aggregated probability value Y for that organ/object segmentation is greater than a fixed threshold value that is predefined in the quality assessment guidelines 130 (e.g., 0.2 for example). The quality assessment component 116 can similarly determine that the individual organ/object segmentation is incorrect (i.e., inaccurate) if the aggregated probability value Y is less than or equal to the fixed threshold probability value, in which case the quality assessment component 116 can characterize the organ/object segmentation as an "outlier." If the deep learning model inference fails or the organ is not visible in the scan, then the organ's auto-segmentation can be considered "missing."

As applied to the global or entire case-level representing the segmentation results data 112 collectively, in some embodiments, the quality assessment component 116 can determine whether the auto-segmentation overall is acceptable or not based on the number of outlier and missing individual segmentations. For example, the quality assessment guidelines 130 may characterize a case as acceptable if the number of organ's auto-segmentations assessed as "acceptable" is greater than the sum of the auto-segmentations assessed as "outlier" and "missing," otherwise the case can be considered as an unacceptable or "outlier case." The abnormality of the auto-segmentation can be indicated in the name of the structure or the structure-set with the segmentation results data 112 when exported in a standard format (e.g., DICOM RTSS) and/or identified/highlighted in a quality assessment report (e.g., quality assessment report 138) attached to the segmented cases in a standard format (DICOM RS).

FIG. 6 depicts a table 600 illustrating example auto-segmentation quality assessment results in accordance with one or more embodiments of the disclosed subject matter. The quality assessment results represented in table 600 represent the measures of quality of individual organ/object segmentations as probability values determined in accordance with Equations 1-3 as discussed above (e.g., Y values). Table 600 illustrates example results of an auto-segmentation model as applied to ten different cases (i.e., ten different medical image exams for different patients). In this example, the auto-segmentation model was configured to segment 8 different anatomical objects, respectively indicated as objects 1-8. The values in the respective cells under each object correspond to the quality measure determined for each object segmentation generated by the auto-segmentation model, wherein the measure corresponds to the final approximated probability values (i.e., the Y values) determined in accordance with Equations 1-3 above. In this example, a threshold probability of 0.2 was applied to characterize outlier segmentations (e.g., any object segmentation with a quality score or Y value smaller than 0.2 was considered inaccurate and thus an outlier). The criteria for characterizing a case as acceptable or failed overall (i.e., an unacceptable overall segmentation) was based on the combined number of outliers and missing segmentations being less than or equal to three. Cells corresponding to outliers are indicated in gray. Cells with a value of zero and denoted in black fill correspond to missing segmentations (e.g., objects that the segmentation model did not recognize and segment at all). In this example, cases 1, 4, 5 and 7-9 resulted in acceptable global quality results and thus passed the quality assessment check. Cases 2-3, 6 and 10 resulted in unacceptable global quality results and thus failed the quality assessment check.

With reference again to FIG. 1, as noted above, the reporting component 118 can generate a quality assessment report 138 that can be presented to a user (e.g., a radiologist, a clinician, etc.) in association with the segmentation results data 112 via a suitable device display (e.g., via rendering component 132), wherein the quality assessment report 138 includes the results of the quality assessment performed by the quality assessment component 116. For example, the quality assessment report 138 can include information regarding the quality of each of the individual organ/object segmentation masks, such as the Y scores illustrated in table 600 and/or another valuation of the accuracy/correctness of the respective segmentation masks determined based on the aggregated feature correspondence values for each organ/object segmentation mask. The quality assessment report 138 can also identify any organ/object segmentation that were deemed to be of deficient quality and thus outliers based on the quality assessment guidelines 130 and the defined outlier criteria. The quality assessment report 138 can also include information regarding the overall or global quality of the segmentation results data 112.

In some embodiments, the alert component 120 can generate one or more alerts 140 based on the quality assessment results satisfying one or more predefined alert criteria defined in the quality assessment guidelines data 130. For example, the alert criteria may be based on the individual organ/segmentation quality measures and/or the global quality measure for the segmentation results data 112. In this regard, depending on the defined alert criteria, the alert component 120 may generate an alert based on one or more individual organ/object segmentation quality measure failing to satisfy a threshold quality measure and/or based on the global quality measure failing to satisfy a defined threshold. The alert component 120 can further include the alerts 140 in the quality assessment report 138 and/or provide the alerts to the clinicians in a separate electronic notification message, thereby calling attention to the clinician's regarding any elements of the segmentation results data 112 considered inaccurate for clinical application.

Figure 7:
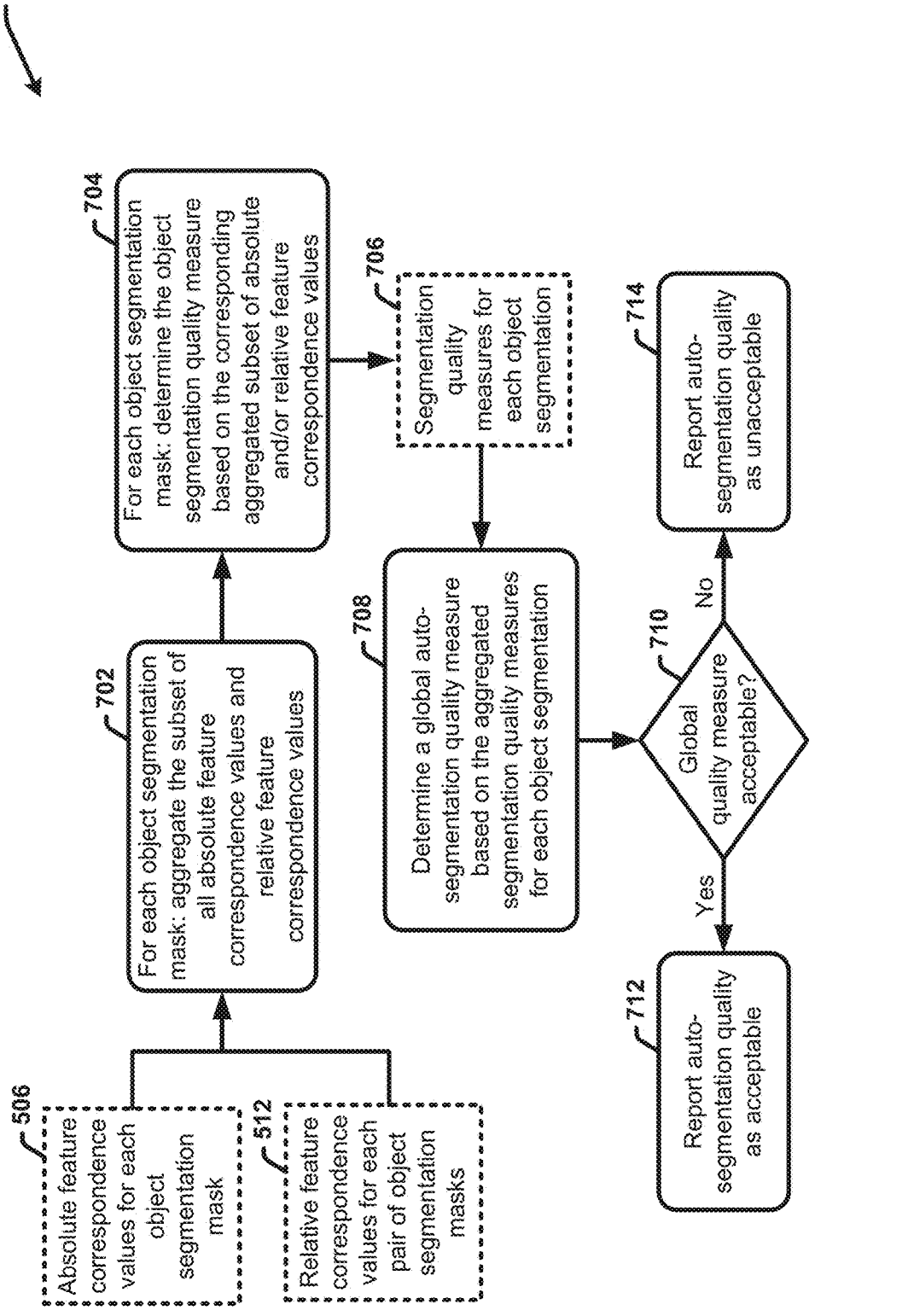
FIG. 7 presents a flow diagram of an example process for assessing the output quality of a multi-organ auto segmentation in accordance with one or more embodiments of the disclosed subject matter.

FIG. 7 presents a flow diagram of an example process 700 for assessing the output quality of a multi-organ auto segmentation in accordance with one or more embodiments of the disclosed subject matter. With reference to FIGS. 1-7, process 700 provides additional details regarding the quality assessment component 116 and steps 402 and 404 of process 400. Process 700 provides an example high-level method for assessing the quality of an auto-segmentation based on the absolute feature correspondence values for each object segmentation mask 506 (determined as described with reference to process 500) and the relative feature correspondence values for each pair of segmentation masks 512 (also determined as described with reference to process 500).

In accordance with process 700, at 702, for each object segmentation mask, the quality assessment component 116 can aggregate the subset of all absolute feature correspondence values and relative feature correspondence values. At 704, for each object segmentation mask, the quality assessment component 116 can determine the object segmentation quality measure based on the corresponding aggregated subset of absolute and/or relative feature correspondence values, resulting in segmentation quality measures for each object segmentation 706. For example, the segmentation quality measure may correspond to an aggregated correspondence value for the respective absolute and relative features included in the subset for each object/organ segmentation. In another example, the segmentation quality measure may correspond to the final approximated probability value (i.e., the Y value) for each segmentation determined in accordance with Equations 1-3. Various other valuations are envisioned based on different aggregation techniques for the respective feature correspondence values.

At 708, the quality assessment component 116 can determine the global auto-segmentation quality measure based on the aggregated segmentation quality measure for each object segmentation. For example, in some implementations, the quality assessment component 116 can determine the global quality measure as the mean quality measure of the respective individual degemination quality measures 706. In another example, the quality assessment component 116 can determine the global quality measure as a function of the number of outliers relative to the number of acceptable individual segmentations. At 710, the quality assessment component 116 determines whether the global quality measure is acceptable or not based on whether the global quality measure satisfies defined acceptability criterion for the segmentation model defined in the quality assessment guidelines 130 (e.g., a threshold global quality value, a maximum number of outliers, etc.). Based on a determination that the global quality measure is acceptable at 710, process 700 proceeds to 712, wherein the reporting component 118 can report the auto-segmentation as acceptable (e.g., accurate enough for clinical application) in the quality assessment report 138. However, based on a determination that the global quality measure is not acceptable at 710, process 700 proceeds to 714, wherein the reporting component 118 can report the auto-segmentation as unacceptable (e.g., not accurate enough for clinical application) in the quality assessment report 138.

Figure 8:
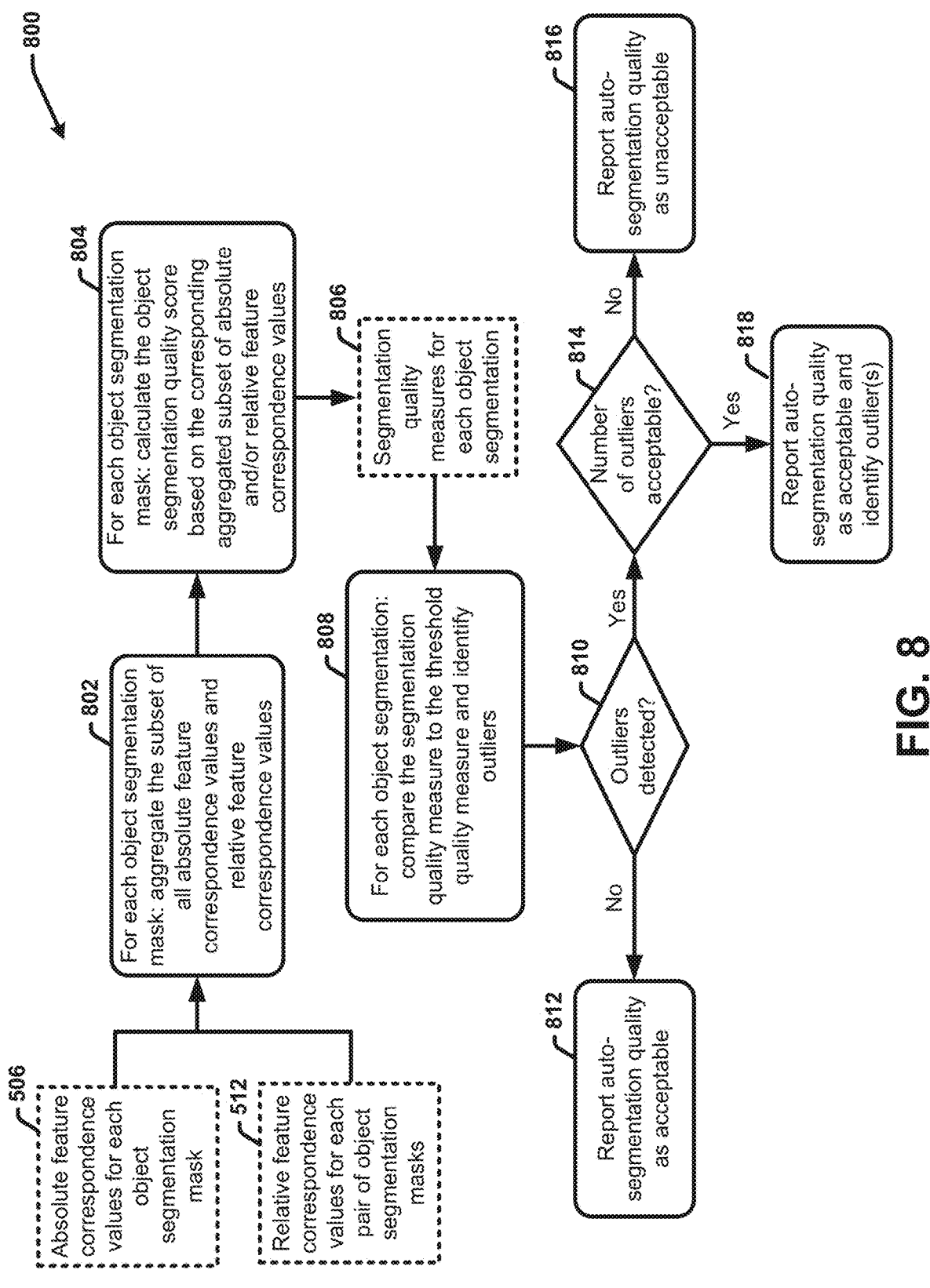
FIG. 8 presents a flow diagram of another example process for assessing the output quality of a multi-organ auto segmentation in accordance with one or more embodiments of the disclosed subject matter.

FIG. 8 presents a flow diagram of another example process 800 for assessing the output quality of a multi-organ auto segmentation in accordance with one or more embodiments of the disclosed subject matter. With reference to FIGS. 1-8, process 800 provides additional details regarding the quality assessment component 116 and steps 402 and 404 of process 400. Process 700 provides another example high-level method for assessing the quality of an auto-segmentation based on the absolute feature correspondence values for each object segmentation mask 506 (determined as described with reference to process 500) and the relative feature correspondence values for each pair of segmentation masks 512 (also determined as described with reference to process 500).

In accordance with process 800, at 802, for each object segmentation mask, the quality assessment component 116 can aggregate the subset of all absolute feature correspondence values and relative feature correspondence values. At 804, for each object segmentation mask, the quality assessment component 116 can determine the object segmentation quality measure based on the corresponding aggregated subset of absolute and/or relative feature correspondence values, resulting in segmentation quality measures for each object segmentation 806. For example, the segmentation quality measure may correspond to an aggregated correspondence value for the respective absolute and relative features included in the subset for each object/organ segmentation. In another example, the segmentation quality measure may correspond to the final approximated probability value (i.e., the Y value) for each segmentation determined in accordance with Equations 1-3. Various other valuations are envisioned based on different aggregation techniques for the respective feature correspondence values.

At 808, for each object segmentation, the quality assessment component 116 can compare the segmentation quality measure to the threshold quality measure and identify any outliers (e.g., that fail to satisfy the threshold quality measure. At 810, the quality assessment component 116 can assess whether any outliers were detected. If no outliers are detected, process 800 process to 812, wherein the reporting component 118 can report the auto-segmentation as acceptable (e.g., accurate enough for clinical application) in the quality assessment report 138. If at 810 the quality assessment component 116 identifies one or more outliers, process 800 proceeds to 814, the quality assessment component 116 determines whether the number of outliers is acceptable for the segmentation model. In this regard, in accordance with process 800, the quality assessment component 116 assesses the overall quality of the segmentation results data 112 based on the number of outliers relative to a defined maximum number of acceptable outliers (e.g., as defined in the quality assessment guidelines 130). It should be appreciated however that various other valuations of the outliers (e.g., including the respective values of the outliers) may be applied in association with assessing the overall quality of the segmentation results. If at 814 the quality assessment component determines that the number of outliers is acceptable, then process 800 proceeds to 818 wherein the reporting component 118 can report the auto-segmentation as acceptable and identify any outliers (e.g., accurate enough for clinical application) in the quality assessment report 138. For example, the quality assessment report can specifically identify the particular organ/object segmentation that were deemed outliers and thus call these outliers to the attention of the clinician for manual review and/or manually contouring. However, based on a determination that the number of outliers is not acceptable at 814, process 800 proceeds to 816, wherein the reporting component 118 can report the auto-segmentation as unacceptable (e.g., not accurate enough for clinical application) in the quality assessment report 138.

Figure 9:
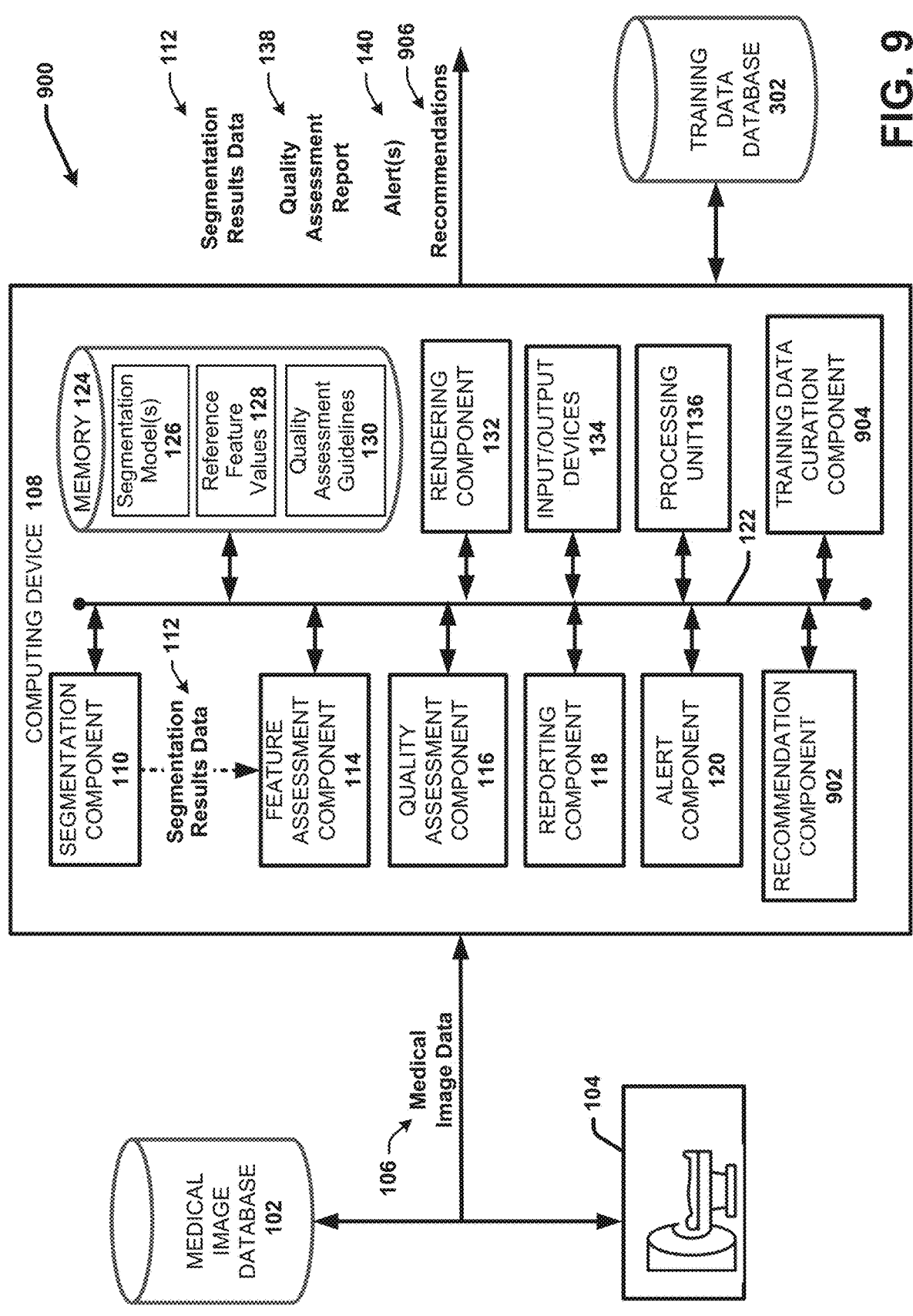
FIG. 9 presents another example system that facilitates automated organ segmentation output quality assessment in accordance with one or more embodiments of the disclosed subject matter.

FIG. 9 presents another example system 900 that facilitates automated organ segmentation output quality assessment in accordance with one or more embodiments of the disclosed subject matter. System 900 is similar to system 100 with the addition of recommendation component 902, training data curation component 904 and training database 302. Repetitive description of like elements employed in respective embodiments is omitted for sake of brevity.

In some embodiments, the recommendation component 902 can determine one or more recommended actions to be performed based on the quality assessment results and provide recommendations 906 to one or more users regarding the recommended actions. For example, in some embodiments, the recommendation component 902 can recommend manual review of the segmentation results data 112 based on the global quality measure and/or one or more of the individual organ/object segmentation quality measures failing to satisfy the acceptable quality measure criteria. Additionally, or alternatively, the recommendation component 902 can determine that the input medical image data 106 may be attributed to some deficiency or error based on the quality assessment results indicating the segmentation results data 112 is significantly inaccurate (e.g., as defined in the quality assessment guidelines). For example, the quality assessment component 116 may apply first criteria for defining the quality assessment results data as being moderately inaccurate (e.g., based on the number of outliers being between 2 and 4) and a second criteria for characterizing the quality assessment results data 112 as being significantly inaccurate so as to indicate potential error or deficiency in the medical image data 106 (e.g., based on the number of outliers exceeding 4). With these embodiments, the recommendation component 902 can recommend the patient be rescanned (e.g., via the medical imaging system 104) to generate new medical image data for the patient for processing by the computing device 108.

The training data curation component 904 can further employ the quality assessment results to identify and collect additional cases for re-training and updating (i.e., optimizing) the performance of the corresponding segmentation models 126. For example, in some embodiments, the training data curation component 904 can be configured to collect the input medical image data for all cases with segmentation results data considered of deficient quality (e.g., based on the global quality measure and/or one or more individual organ/object segmentation quality measures) and add the input medical image data to the corresponding training dataset included in the training data database 302. The training data curation component 904 can also include the segmentation results data 112 and the associated quality assessment report 138 generated for each of the outlier or deficient cases with the input medical image data in the training data database 302.

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, procedural programming languages, such as the "C" programming language or similar programming languages, and machine-learning programming languages such as like CUDA, Python, Tensorflow, PyTorch, and the like. The computer readable program instructions can execute entirely on the user's computer, partly on the user's computer, as a stand-alone software package, partly on the user's computer and partly on a remote computer or entirely on the remote computer or server using suitable processing hardware. In the latter scenario, the remote computer can be connected to the user's computer through any type of network, including a local area network (LAN) or a wide area network (WAN), or the connection can be made to an external computer (for example, through the Internet using an Internet Service Provider). In various embodiments involving machine-learning programming instructions, the processing hardware can include one or more graphics processing units (GPUs), central processing units (CPUs), and the like. For example, one or more of the disclosed machine-learning models (e.g., the image transformation model 908, the deep learning network 1010 and/or combinations thereof) may be written in a suitable machine-learning programming language and executed via one or more GPUs, CPUs or combinations thereof. In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
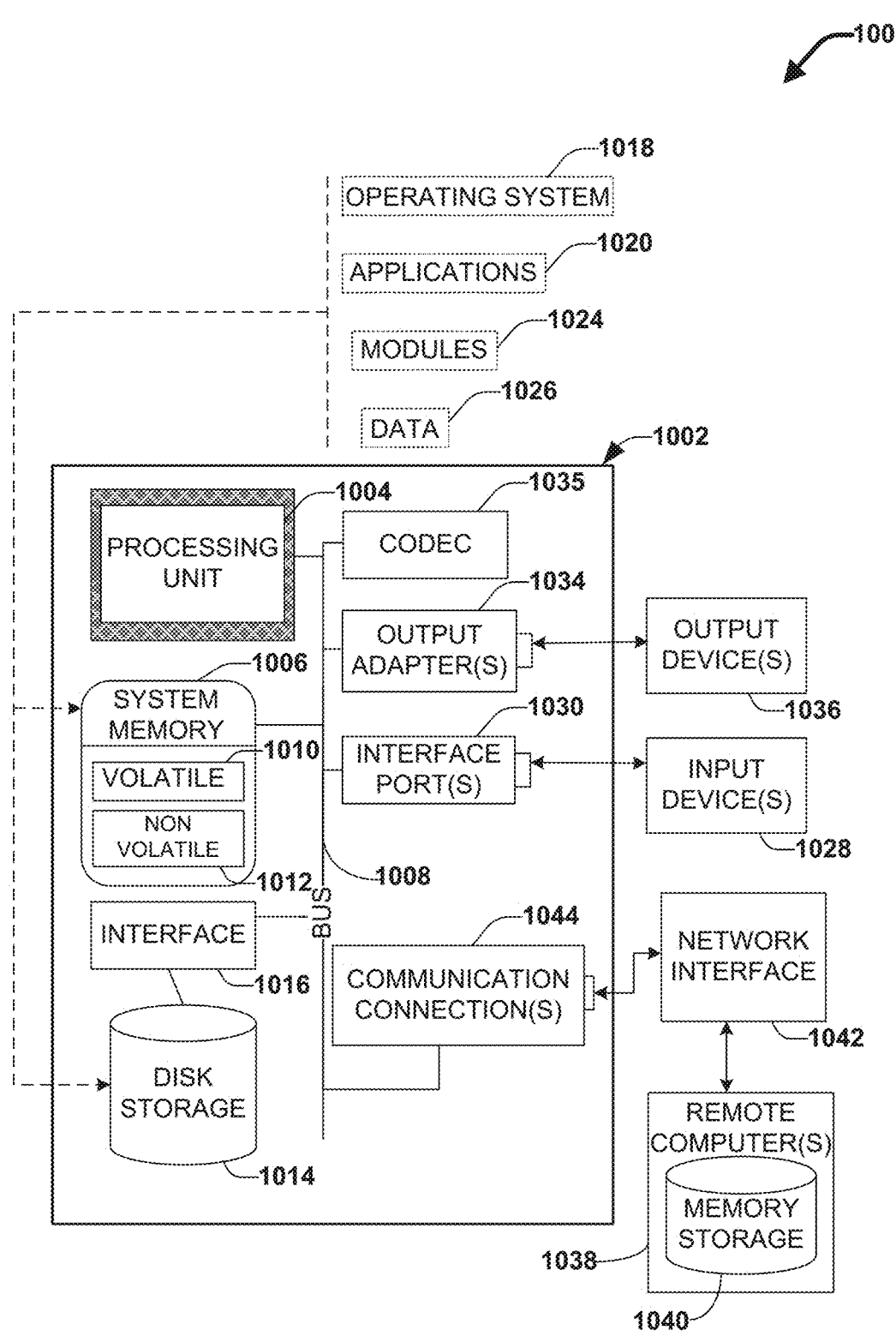
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors, one or more GPUs, CPUs, and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1094), and Small Computer Systems Interface (SCSI).

The system memory 1006 includes volatile memory 1010 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1010 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1014 to the system bus 1008, a removable or non-removable interface is typically used, such as interface 1016. It is appreciated that disk storage 1014 can store information related to a user. Such information might be stored at or provided to a server or to an application running on a user device. In one embodiment, the user can be notified (e.g., by way of output device(s) 1036) of the types of information that are stored to disk storage 1014 or transmitted to the server or application. The user can be provided the opportunity to opt-in or opt-out of having such information collected or shared with the server or application (e.g., by way of input from input device(s) 1028).

It is to be appreciated that FIG. 10 describes software that acts as an intermediary between users and the basic computer resources described in the suitable operating environment 1000. Such software includes an operating system 1018. Operating system 1018, which can be stored on disk storage 1014, acts to control and allocate resources of the computer 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

A user enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer-executable components; and
a processor that executes the computer-executable components stored in the memory, wherein the computer-executable components comprise:
a feature assessment component that determines current values of defined features of respective segmentation masks generated for different anatomical structures included in medical image data via auto-segmentation of the medical image data;
a quality assessment component that determines respective measures of correspondence between the current values and corresponding reference values determined for the defined features and determines one or more measures of quality of the auto-segmentation based on the respective measures of correspondence, wherein the one or more measures of quality comprise structure-specific quality measures for the respective segmentation masks that reflect measures of quality of the respective segmentation masks, and wherein quality assessment component determines the structure-specific quality measures for each of the respective segmentation masks based on aggregated measures of correspondence for a plurality of the defined features as associated with each of the respective segmentation masks; and
a reporting component that generates quality assessment report data for the auto-segmentation comprising the one or more measures of quality.

2. The system of claim 1, wherein the one or more measures of quality comprise a set quality measure for a specific structure set represented by a group of the segmentation masks, and wherein the reporting component integrates the quality measure with the specific structure set in a standard clinical data format.

3. The system of claim 1, wherein the one or more measures of quality further comprise an overall measure of quality of the auto-segmentation determined by the quality assessment component based on aggregation of the structure-specific quality measures.

4. The system of claim 1, wherein the defined features comprise absolute features representing independent characteristics of the respective segmentation masks.

5. The system of claim 4, wherein the absolute features comprise one or more geometrical features related to a size or shape of the respective segmentation masks.

6. The system of claim 4, wherein the absolute features comprise one or more latent features of the respective segmentation masks.

7. The system of claim 4, wherein the defined features further comprise relative features representing relative characteristics of different pairs of the respective segmentation masks.

8. The system of claim 7, wherein the relative characteristics comprise relative distances between each segmentation mask included in the different pairs.

9. The system of claim 1, wherein the computer-executable components further comprise:

a rendering component that presents the respective segmentation masks and the quality assessment report data via a device display associated with one or more clinical entities in association with employing the respective segmentation masks to facilitate a clinical procedure on a patient from which the medical image data was captured.

10. The system of claim 1, wherein the computer-executable components further comprise:

an alert component that generates alert data based on the one or more measures of quality failing to satisfy a threshold quality measure and provides the alert data to one or more devices associated with one or more clinicians.

11. The system of claim 10, wherein the alert data relates to a specific structure or structure set represented by a segmentation mask or group of the segmentation masks, and wherein the alert component integrates the alert data with the specific structure or structure set in a standard clinical data format.

12. The system of claim 1, wherein the computer-executable components further comprise:

a recommendation component that determines one or more clinical workflow actions to be performed based on the one or more measures of quality failing to satisfy a threshold quality measure and provides recommendation data identifying the one or more clinical workflow actions to one or more devices associated with one or more clinicians.

13. The system of claim 1, wherein the feature assessment component determines the corresponding reference values for the defined features based on ground truth organ segmentation data for the different anatomical structures as depicted in training medical image data.

14. A method, comprising:

determining, by a system comprising a processor, current values of defined features of respective segmentation masks generated for different anatomical structures included in medical image data via auto-segmentation of the medical image data;

determining, by the system, respective measures of correspondence between the current values and corresponding reference values determined for the defined features;

determining, by the system, one or more measures of quality of the auto-segmentation based on the respective measures of correspondence, wherein the one or more measures of quality comprise structure-specific quality measures for the respective segmentation masks that reflect measures of quality of the respective segmentation masks, and wherein determining the structure-specific quality measures comprises:

for each segmentation mask of the respective segmentation masks, determining a corresponding structure-specific quality measure for the segmentation mask based on a group of the respective measures of correspondence for a plurality of the defined features as associated with the segmentation mask; and generating, by the system, quality assessment report data for the auto-segmentation comprising the one or more measures of quality.

15. The method of claim 14, wherein determining the one or more measures of quality comprises determining a set quality measure for a specific structure set represented by a group of the segmentation masks, and wherein the generating comprises integrating the quality measure with the specific structure set in a standard clinical data format.

16. The method of claim 14, further comprising:

generating, by the system, alert data based on the one or more measures of quality failing to satisfy a threshold quality measure; and providing, by the system, the alert data to one or more devices associated with one or more clinicians.

17. The method of claim 14, wherein the alert data relates to a specific structure or structure set represented by a segmentation mask or group of the segmentation masks, and wherein the generating the alert data comprises integrating the alert data with the specific structure or structure set in a standard clinical data format.

18. The method of claim 14, wherein the one or more measures of quality further comprise an overall measure of quality of the auto-segmentation determined based on aggregation of two or more structure-specific quality measures.

19. A non-transitory machine-readable storage medium, comprising executable instructions that, when executed by a processor, facilitate performance of operations, comprising:

determining current values of defined features of respective segmentation masks generated for different anatomical structures included in medical image data via auto-segmentation of the medical image data;

determining respective measures of correspondence between the current values and corresponding reference values determined for the defined features;

determining one or more measures of quality of the auto-segmentation based on the respective measures of correspondence, wherein the one or more measures of quality comprise structure-specific quality measures for the respective segmentation masks that reflect measures of quality of the respective segmentation masks, and wherein determining the structure-specific quality measures comprises:

for each segmentation mask of the respective segmentation masks, determining a corresponding structure-specific quality measure for the segmentation mask based on a group of the respective measures of correspondence for a plurality of the defined features as associated with the segmentation mask; and generating quality assessment report data for the auto-segmentation comprising the one or more measures of quality.

20. The non-transitory machine-readable storage medium of claim 19, wherein the one or more measures of quality further comprise an overall measure of quality of the auto-segmentation determined based on aggregation of two or more structure-specific quality measures.

* * * * *